United States Patent
Sackler

(10) Patent No.: US 9,895,317 B2
(45) Date of Patent: *Feb. 20, 2018

(54) TAMPER RESISTANT SOLID ORAL DOSAGE FORMS

(71) Applicant: Purdue Pharma L.P., Stamford, CT (US)

(72) Inventor: Richard S. Sackler, Greenwich, CT (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,039

(22) Filed: Oct. 3, 2016

(65) Prior Publication Data

US 2017/0020820 A1  Jan. 26, 2017

Related U.S. Application Data

(62) Division of application No. 14/992,789, filed on Jan. 11, 2016, now Pat. No. 9,707,180, which is a division
(Continued)

(51) Int. Cl.
*A61K 9/28* (2006.01)
*A61K 9/20* (2006.01)
(Continued)

(52) U.S. Cl.
CPC .......... *A61K 9/2086* (2013.01); *A61K 9/0053* (2013.01); *A61K 9/2004* (2013.01); *A61K 9/2013* (2013.01); *A61K 9/2095* (2013.01); *A61K 9/28* (2013.01); *A61K 9/2866* (2013.01); *A61K 9/5078* (2013.01); *A61K 9/5089* (2013.01); *A61K 31/135* (2013.01); *A61K 31/485* (2013.01); *A61K 45/06* (2013.01)

(58) Field of Classification Search
None
See application file for complete search history.

(56) References Cited

U.S. PATENT DOCUMENTS

| 3,065,143 A | 11/1962 | Christenson et al. |
| 3,096,248 A | 7/1963 | Rudzki |

(Continued)

FOREIGN PATENT DOCUMENTS

| CA | 2569743 | 12/2005 |
| EP | 0111144 | 10/1983 |

(Continued)

OTHER PUBLICATIONS

Techinical Sheet for EUDRAGIT L 100-55 [online] (2015) obtained from the URL <https://www.higuchi-inc.co.jp/pharma/excipient/eudragit/pdf/detail _eudragitL100-55.pdf>.*
(Continued)

*Primary Examiner* — John Pak
*Assistant Examiner* — Daniel Branson
(74) *Attorney, Agent, or Firm* — Lowenstein Sandler LLP

(57) ABSTRACT

Disclosed in certain embodiments is a solid oral dosage form comprising: (a) an inert tamper resistant core; and (b) a coating surrounding the core, the coating comprising an active agent.

24 Claims, 2 Drawing Sheets

Related U.S. Application Data of application No. 13/997,560, filed as application No. PCT/IB2011/003162 on Dec. 22, 2011, now Pat. No. 9,233,073.

(60) Provisional application No. 61/426,903, filed on Dec. 23, 2010.

(51) Int. Cl.
*A61K 31/285* (2006.01)
*A61K 9/00* (2006.01)
*A61K 9/50* (2006.01)
*A61K 31/135* (2006.01)
*A61K 31/485* (2006.01)
*A61K 45/06* (2006.01)

(56) References Cited

U.S. PATENT DOCUMENTS

| | | |
|---|---|---|
| 3,133,132 A | 5/1964 | Loeb et al. |
| 3,173,876 A | 3/1965 | Zobrist et al. |
| 3,260,646 A | 7/1966 | Paulsen |
| 3,276,586 A | 10/1966 | Rosaen |
| 3,400,197 A | 9/1968 | Lippman |
| 3,541,005 A | 11/1970 | Strathmann et al. |
| 3,541,006 A | 11/1970 | Bixler et al. |
| 3,546,876 A | 12/1970 | Fokker et al. |
| 3,845,770 A | 11/1974 | Theeuwes et al. |
| 3,879,555 A | 4/1975 | Pachter et al. |
| 3,916,889 A | 11/1975 | Russell |
| 3,965,256 A | 6/1976 | Leslie |
| 3,980,766 A | 9/1976 | Shaw et al. |
| 4,063,064 A | 12/1977 | Saunders et al. |
| 4,070,494 A | 1/1978 | Hollmeister et al. |
| 4,088,864 A | 5/1978 | Theeuwes et al. |
| 4,160,020 A | 7/1979 | Ayer et al. |
| 4,175,119 A | 11/1979 | Porter |
| 4,200,098 A | 4/1980 | Ayer et al. |
| 4,235,870 A | 11/1980 | Leslie |
| 4,285,987 A | 8/1981 | Ayer et al. |
| 4,293,539 A | 10/1981 | Ludwig et al. |
| 4,366,310 A | 12/1982 | Leslie |
| 4,385,057 A | 5/1983 | Bjork et al. |
| 4,389,393 A | 6/1983 | Schor et al. |
| 4,424,205 A | 1/1984 | LaHann et al. |
| 4,443,428 A | 4/1984 | Oshlack et al. |
| 4,457,933 A | 7/1984 | Gordon et al. |
| 4,459,278 A | 7/1984 | Porter |
| 4,588,580 A | 5/1986 | Gale et al. |
| 4,599,342 A | 7/1986 | LaHann |
| 4,610,870 A | 9/1986 | Jain et al. |
| 4,612,008 A | 9/1986 | Wong et al. |
| 4,629,623 A | 12/1986 | Balazs et al. |
| 4,666,705 A | 5/1987 | DeCrosta et al. |
| 4,764,378 A | 8/1988 | Keith et al. |
| 4,765,989 A | 8/1988 | Wong et al. |
| 4,769,372 A | 9/1988 | Kreek |
| 4,785,000 A | 11/1988 | Kreek et al. |
| 4,806,341 A | 2/1989 | Chien et al. |
| 4,812,446 A | 3/1989 | Brand |
| 4,834,984 A | 5/1989 | Goldie et al. |
| 4,844,909 A | 7/1989 | Goldie et al. |
| 4,861,598 A | 8/1989 | Oshlack |
| 4,957,681 A | 9/1990 | Klimesch et al. |
| 4,970,075 A | 11/1990 | Oshlack |
| 4,990,341 A | 2/1991 | Goldie et al. |
| 4,992,277 A | 2/1991 | Sangekar et al. |
| 5,026,556 A | 6/1991 | Drust et al. |
| 5,059,600 A | 10/1991 | Gawin et al. |
| 5,069,909 A | 12/1991 | Sharma et al. |
| 5,111,942 A | 5/1992 | Bernardin |
| 5,113,585 A | 5/1992 | Rogers et al. |
| 5,114,942 A | 5/1992 | Gawin et al. |
| 5,130,311 A | 7/1992 | Guillaumet et al. |
| 5,149,538 A | 9/1992 | Granger et al. |
| 5,169,645 A | 12/1992 | Shukla et al. |
| 5,202,128 A | 4/1993 | Morella et al. |
| 5,215,758 A | 6/1993 | Krishnamurthy |
| 5,225,199 A | 7/1993 | Hidaka et al. |
| 5,232,685 A | 8/1993 | Speck et al. |
| 5,232,934 A | 8/1993 | Downs |
| 5,240,711 A | 8/1993 | Hille et al. |
| 5,266,331 A | 11/1993 | Oshlack et al. |
| 5,273,758 A | 12/1993 | Royce |
| 5,273,760 A | 12/1993 | Oshlack et al. |
| 5,286,493 A | 2/1994 | Oshlack et al. |
| 5,290,816 A | 3/1994 | Blumberg |
| 5,300,302 A | 4/1994 | Tachon et al. |
| 5,321,012 A | 6/1994 | Mayer et al. |
| 5,324,351 A | 6/1994 | Oshlack et al. |
| 5,330,766 A | 7/1994 | Morella et al. |
| 5,356,467 A | 10/1994 | Oshlack et al. |
| 5,376,705 A | 12/1994 | Leys et al. |
| 5,378,474 A | 1/1995 | Morella et al. |
| 5,399,351 A | 3/1995 | Leschiner et al. |
| 5,403,868 A | 4/1995 | Reid et al. |
| 5,409,944 A | 4/1995 | Black et al. |
| 5,411,745 A | 5/1995 | Oshlack et al. |
| 5,422,123 A | 6/1995 | Conte et al. |
| 5,425,950 A | 6/1995 | Dandiker et al. |
| 5,436,265 A | 7/1995 | Black et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,500,227 A | 3/1996 | Oshlack et al. |
| 5,502,058 A | 3/1996 | Mayer et al. |
| 5,505,959 A | 4/1996 | Tachon et al. |
| 5,508,042 A | 4/1996 | Oshlack et al. |
| 5,508,043 A | 4/1996 | Krishnamurthy |
| 5,510,368 A | 4/1996 | Lau et al. |
| 5,514,680 A | 5/1996 | Weber et al. |
| 5,521,213 A | 5/1996 | Prasit et al. |
| 5,489,439 A | 6/1996 | Bola |
| 5,536,752 A | 7/1996 | Ducharme et al. |
| 5,549,912 A | 8/1996 | Oshlack et al. |
| 5,549,913 A | 8/1996 | Colombo et al. |
| 5,550,142 A | 8/1996 | Ducharme et al. |
| 5,552,422 A | 9/1996 | Gauthier et al. |
| 5,556,838 A | 9/1996 | Mayer et al. |
| 5,567,439 A | 10/1996 | Myers et al. |
| 5,580,578 A | 12/1996 | Oshlack et al. |
| 5,593,695 A | 1/1997 | Merrill et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,593,694 A | 6/1997 | Hayashida et al. |
| 5,639,476 A | 6/1997 | Oshlack et al. |
| 5,639,789 A | 6/1997 | Lau et al. |
| 5,654,005 A | 8/1997 | Chen et al. |
| 5,656,295 A | 8/1997 | Oshlack et al. |
| 5,667,805 A | 9/1997 | Merrill et al. |
| 5,672,360 A | 9/1997 | Sackler et al. |
| 5,676,972 A | 10/1997 | Galiatsatos et al. |
| 5,679,650 A | 10/1997 | Fukunaga et al. |
| 5,681,585 A | 10/1997 | Oshlack et al. |
| 5,695,781 A | 12/1997 | Zhang et al. |
| 5,702,725 A | 12/1997 | Merrill et al. |
| 5,730,716 A | 3/1998 | Beck et al. |
| 5,741,524 A | 4/1998 | Staniforth et al. |
| 5,762,963 A | 6/1998 | Byas-Smith |
| 5,766,623 A | 6/1998 | Aryes et al. |
| 5,788,987 A | 8/1998 | Busetti et al. |
| 5,811,126 A | 9/1998 | Krishnamurthy |
| 5,811,388 A | 9/1998 | Friend et al. |
| 5,814,336 A | 9/1998 | Kelm et al. |
| 5,837,379 A | 11/1998 | Chen et al. |
| 5,843,480 A | 12/1998 | Miller et al. |
| 5,849,240 A | 12/1998 | Miller et al. |
| 5,866,164 A | 2/1999 | Kuczynski et al. |
| 5,879,705 A | 3/1999 | Heafield et al. |
| 5,891,471 A | 4/1999 | Miller et al. |
| 5,891,919 A | 4/1999 | Blum et al. |

(56) References Cited

U.S. PATENT DOCUMENTS

| | | |
|---|---|---|
| 5,914,131 A | 6/1999 | Miller et al. |
| 5,945,125 A | 8/1999 | Kin |
| 5,948,787 A | 9/1999 | Merrill et al. |
| 5,958,452 A | 9/1999 | Oshlack et al. |
| 5,958,459 A | 9/1999 | Chasin et al. |
| 5,965,163 A | 9/1999 | Miller et al. |
| 5,965,161 A | 10/1999 | Oshlack et al. |
| 5,968,551 A | 10/1999 | Oshlack et al. |
| 6,024,982 A | 2/2000 | Oshlack et al. |
| 6,103,261 A | 8/2000 | Chasin et al. |
| 6,120,751 A | 9/2000 | Unger |
| 6,124,282 A | 9/2000 | Sellers et al. |
| 6,126,969 A | 10/2000 | Shah et al. |
| 6,136,864 A | 10/2000 | Nichols et al. |
| 6,143,322 A | 11/2000 | Sackler et al. |
| 6,153,621 A | 11/2000 | Hamann |
| 6,162,467 A | 12/2000 | Miller et al. |
| 6,210,712 B1 | 4/2001 | Edgren et al. |
| 6,210,714 B1 | 4/2001 | Oshlack et al. |
| 6,223,075 B1 | 4/2001 | Beck et al. |
| 6,228,863 B1 | 5/2001 | Palermo et al. |
| 6,245,357 B1 | 6/2001 | Edgren et al. |
| 6,251,430 B1 | 6/2001 | Zhang et al. |
| 6,277,398 B1 | 8/2001 | Caruso |
| 6,294,194 B1 | 9/2001 | Horhota et al. |
| 6,309,668 B1 | 10/2001 | Bastin et al. |
| 6,348,469 B1 | 2/2002 | Seth |
| 6,352,721 B1 | 3/2002 | Faour |
| 6,365,185 B1 | 4/2002 | Ritschel et al. |
| 6,372,254 B1 | 4/2002 | Ting et al. |
| 6,375,957 B1 | 4/2002 | Kaiko et al. |
| 6,403,056 B1 | 6/2002 | Unger |
| 6,419,954 B1 | 7/2002 | Chu |
| 6,419,960 B1 | 7/2002 | Krishnamurthy et al. |
| 6,436,441 B1 | 8/2002 | Sako et al. |
| 6,440,464 B1 | 8/2002 | Hsia et al. |
| 6,455,537 B1 | 9/2002 | Cooper |
| 6,485,748 B1 | 11/2002 | Chen et al. |
| 6,488,963 B1 | 12/2002 | McGinity |
| 6,491,949 B2 | 12/2002 | Faour et al. |
| 6,559,159 B2 | 5/2003 | Carroll et al. |
| 6,572,885 B2 | 6/2003 | Oshlack et al. |
| 6,593,367 B1 | 7/2003 | Dewey et al. |
| 6,627,635 B2 | 9/2003 | Palermo et al. |
| 6,696,088 B2 | 2/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,761,895 B2 | 7/2004 | Sawada et al. |
| 6,808,720 B2 | 10/2004 | Unger |
| 6,955,821 B2 | 10/2005 | Davis et al. |
| 6,987,082 B2 | 1/2006 | Tijsma et al. |
| 6,995,169 B2 | 2/2006 | Chapleo et al. |
| RE39,239 E | 8/2006 | Busetti et al. |
| 7,141,250 B2 | 11/2006 | Oshlack et al. |
| 7,144,587 B2 | 12/2006 | Oshlack et al. |
| 7,157,103 B2 | 1/2007 | Sackler |
| 7,201,920 B2 | 4/2007 | Kumar et al. |
| 7,276,250 B2 | 10/2007 | Baichwal et al. |
| 7,332,182 B2 | 2/2008 | Sackler |
| 7,399,488 B2 | 7/2008 | Hirsch et al. |
| 7,510,726 B2 | 3/2009 | Kumar et al. |
| 7,718,194 B2 | 5/2010 | Chenevier et al. |
| 7,727,557 B2 | 6/2010 | Sackler |
| 7,776,314 B2 | 8/2010 | Bartholomaus |
| 7,842,307 B2 | 11/2010 | Oshlack et al. |
| 7,842,311 B2 | 11/2010 | Oshlack et al. |
| 7,943,174 B2 | 5/2011 | Oshlack et al. |
| 7,981,439 B2 | 7/2011 | Kumar et al. |
| 8,017,148 B2 | 9/2011 | Sackler |
| 8,075,872 B2 | 12/2011 | Arkenau-Maric et al. |
| 8,101,630 B2 | 1/2012 | Kumar et al. |
| 8,114,383 B2 | 2/2012 | Bartholomaus |
| 8,114,384 B2 | 2/2012 | Arkenau et al. |
| 8,143,267 B2 | 3/2012 | Burch et al. |
| 8,192,722 B2 | 6/2012 | Arkenau-Maric et al. |
| 8,193,209 B2 | 6/2012 | Burch et al. |
| 8,293,277 B2 | 10/2012 | Swanson et al. |
| 8,309,060 B2 | 11/2012 | Bartholomaus et al. |
| 8,323,692 B2 | 12/2012 | Frisbee |
| 8,337,888 B2 | 12/2012 | Wright et al. |
| 8,389,007 B2 | 3/2013 | Wright et al. |
| 8,394,408 B2 | 3/2013 | Han et al. |
| 8,409,616 B2 | 4/2013 | Kumar et al. |
| 8,524,275 B2 | 9/2013 | Oshlack et al. |
| 8,529,948 B1 | 9/2013 | Wright et al. |
| 8,551,520 B2 | 10/2013 | Oshlack et al. |
| 8,609,143 B2 | 12/2013 | Fischer et al. |
| 8,609,683 B2 | 12/2013 | Wright et al. |
| 8,617,600 B2 | 12/2013 | Bhatt et al. |
| 8,637,540 B2 | 1/2014 | Kumar et al. |
| 8,647,667 B2 | 2/2014 | Oshlack et al. |
| 8,652,497 B2 | 2/2014 | Sackler |
| 8,652,515 B2 | 2/2014 | Sackler |
| 8,652,529 B2 | 2/2014 | Guimberteau et al. |
| 8,871,265 B2 | 10/2014 | Wright et al. |
| 8,999,961 B2 | 4/2015 | Wright et al. |
| 9,034,376 B2 | 5/2015 | Wright et al. |
| 9,040,084 B2 | 5/2015 | Wright et al. |
| 9,044,435 B2 | 6/2015 | Wright et al. |
| 9,060,976 B2 | 6/2015 | Wright et al. |
| 9,233,073 B2 | 1/2016 | Sackler |
| 2001/0031278 A1 | 10/2001 | Oshlack et al. |
| 2002/0028240 A1 | 3/2002 | Sawada et al. |
| 2002/0187192 A1 | 12/2002 | Joshi et al. |
| 2003/0004177 A1 | 1/2003 | Kao et al. |
| 2003/0021841 A1 | 1/2003 | Matharu et al. |
| 2003/0026838 A1 | 2/2003 | Farrell |
| 2003/0035839 A1 | 2/2003 | Hirsh et al. |
| 2003/0059471 A1 | 3/2003 | Compton et al. |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0082230 A1 | 5/2003 | Baichwal et al. |
| 2003/0091625 A1 | 5/2003 | Hariharan et al. |
| 2003/0092724 A1 | 5/2003 | Kao et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0126428 A1 | 7/2003 | Liu et al. |
| 2003/0170181 A1 | 9/2003 | Midha |
| 2003/0190362 A1 | 10/2003 | Sackler et al. |
| 2003/0206954 A1 | 11/2003 | Lerner et al. |
| 2003/0232081 A1 | 12/2003 | Doshi et al. |
| 2004/0010000 A1 | 1/2004 | Ayer et al. |
| 2004/0047907 A1 | 3/2004 | Oshlack et al. |
| 2004/0110781 A1 | 6/2004 | Harmon et al. |
| 2004/0126428 A1 | 7/2004 | Hughes et al. |
| 2004/0131552 A1 | 7/2004 | Boehm |
| 2004/0151791 A1 | 8/2004 | Mayo-Alvarez et al. |
| 2004/0202717 A1 | 10/2004 | Mehtha |
| 2004/0224020 A1 | 11/2004 | Schoenhard |
| 2004/0228802 A1 | 11/2004 | Chang et al. |
| 2004/0241234 A1 | 12/2004 | Vikov |
| 2004/0253310 A1 | 12/2004 | Fischer et al. |
| 2004/0266807 A1 | 12/2004 | Oshlack et al. |
| 2005/0020613 A1 | 1/2005 | Boehm et al. |
| 2005/0031546 A1 | 2/2005 | Bartholomaus et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0112201 A1 | 5/2005 | Baichwal et al. |
| 2005/0118267 A1 | 6/2005 | Baichwal et al. |
| 2005/0158382 A1 | 7/2005 | Cruz et al. |
| 2005/0163717 A1 | 7/2005 | Anderson et al. |
| 2005/0186139 A1 | 8/2005 | Bartholomaeus et al. |
| 2005/0214223 A1 | 9/2005 | Bartholomaeus et al. |
| 2005/0236741 A1 | 10/2005 | Arkenau et al. |
| 2005/0276853 A1 | 12/2005 | Baichwal et al. |
| 2006/0002860 A1 | 1/2006 | Bartholomaus et al. |

(56) References Cited

U.S. PATENT DOCUMENTS

| | | |
|---|---|---|
| 2006/0018837 A1 | 1/2006 | Preston et al. |
| 2006/0039864 A1 | 2/2006 | Bartholomaus et al. |
| 2006/0165790 A1 | 7/2006 | Walden et al. |
| 2006/0188447 A1 | 8/2006 | Arkenau-Maric et al. |
| 2006/0193782 A1 | 8/2006 | Bartholomaus et al. |
| 2006/0210631 A1 | 9/2006 | Patel et al. |
| 2006/0240107 A1 | 10/2006 | Lenaerts |
| 2006/0251721 A1 | 11/2006 | Cruz et al. |
| 2007/0003616 A1 | 1/2007 | Arkenau-Maric et al. |
| 2007/0003617 A1 | 1/2007 | Fischer et al. |
| 2007/0020335 A1 | 1/2007 | Chen et al. |
| 2007/0110807 A1 | 5/2007 | Vergnault et al. |
| 2007/0166234 A1 | 7/2007 | Kumar et al. |
| 2007/0183980 A1 | 8/2007 | Arkenau-Maric et al. |
| 2007/0224129 A1 | 9/2007 | Guimberteau et al. |
| 2007/0264327 A1 | 11/2007 | Kumar et al. |
| 2008/0026060 A1 | 1/2008 | Zerbe et al. |
| 2008/0057123 A1 | 3/2008 | Grenier et al. |
| 2008/0063725 A1 | 3/2008 | Guimbertau et al. |
| 2008/0090892 A1 | 4/2008 | Casteel et al. |
| 2008/0095843 A1 | 4/2008 | Nutalapati et al. |
| 2008/0107732 A1 | 5/2008 | Dharmadhikari et al. |
| 2008/0147044 A1 | 6/2008 | Palmer et al. |
| 2008/0175908 A1 | 7/2008 | Liu et al. |
| 2008/0176955 A1 | 7/2008 | Heck et al. |
| 2008/0187581 A1 | 8/2008 | Gore et al. |
| 2008/0233197 A1* | 9/2008 | Matthews ............ A61K 9/4808 424/490 |
| 2008/0254123 A1 | 10/2008 | Fischer et al. |
| 2008/0260815 A1 | 10/2008 | Hayes et al. |
| 2008/0260824 A1 | 10/2008 | Nangia et al. |
| 2008/0311191 A1 | 12/2008 | Nangia et al. |
| 2009/0011019 A1 | 1/2009 | Jahagirdar et al. |
| 2009/0022798 A1 | 1/2009 | Rosenberg et al. |
| 2009/0081290 A1 | 3/2009 | McKenna et al. |
| 2009/0169587 A1 | 7/2009 | Baichwal et al. |
| 2009/0215808 A1 | 8/2009 | Yum et al. |
| 2009/0232885 A1 | 9/2009 | Venkatesh et al. |
| 2010/0015222 A1 | 1/2010 | Han et al. |
| 2010/0015223 A1 | 1/2010 | Cailly-Dufestel et al. |
| 2010/0221293 A1 | 9/2010 | Cruz et al. |
| 2011/0020451 A1 | 1/2011 | Bartholomaus et al. |
| 2011/0262532 A1 | 10/2011 | Oshlack et al. |
| 2012/0164220 A1 | 6/2012 | Huang |
| 2013/0209525 A1 | 8/2013 | Cruz et al. |
| 2013/0217716 A1 | 8/2013 | Wright et al. |
| 2013/0245055 A1 | 9/2013 | Wright et al. |
| 2014/0056979 A1 | 2/2014 | Huang |
| 2014/0213606 A1 | 7/2014 | Wright et al. |
| 2014/0371257 A1 | 12/2014 | Wright et al. |
| 2015/0005331 A1 | 1/2015 | Wright et al. |
| 2015/0031718 A1 | 1/2015 | Wright et al. |
| 2015/0140083 A1 | 5/2015 | Wright et al. |
| 2015/0147391 A1 | 5/2015 | Wright et al. |
| 2015/0148319 A1 | 5/2015 | Wright et al. |
| 2015/0182628 A1 | 7/2015 | Wright et al. |

FOREIGN PATENT DOCUMENTS

| | | |
|---|---|---|
| EP | 0318262 | 5/1989 |
| EP | 0661045 | 5/1995 |
| EP | 698389 | 2/1996 |
| EP | 0647448 | 2/2001 |
| EP | 1293195 | 3/2003 |
| EP | 1897545 | 12/2008 |
| EP | 2457563 | 5/2012 |
| JP | 2005-501067 | 1/2005 |
| JP | 2006-506374 | 2/2006 |
| JP | 2007-501201 | 1/2007 |
| JP | 2010-501543 | 1/2010 |
| KR | 10-2007-0111510 | 11/2007 |
| WO | 01/07950 | 6/1991 |
| WO | 1993/10765 | 6/1993 |
| WO | 95/20947 | 8/1995 |
| WO | 97/12605 | 4/1997 |
| WO | 97/37689 | 10/1997 |
| WO | 97/48385 | 12/1997 |
| WO | 97/49384 | 12/1997 |
| WO | 99/20255 | 4/1999 |
| WO | 99/32119 | 7/1999 |
| WO | 99/32120 | 7/1999 |
| WO | 99/44591 | 9/1999 |
| WO | 2000/033835 | 6/2000 |
| WO | 2001/008661 | 2/2001 |
| WO | 2001/056544 | 8/2001 |
| WO | 2001/058447 | 8/2001 |
| WO | 2001/076576 | 10/2001 |
| WO | 2002/036099 | 5/2002 |
| WO | 2002/087558 | 11/2002 |
| WO | 2002/094254 | 11/2002 |
| WO | 2003/013479 | 2/2003 |
| WO | 2003/015531 | 2/2003 |
| WO | 2003/024430 | 3/2003 |
| WO | 2003/026743 | 4/2003 |
| WO | 2003/035029 | 5/2003 |
| WO | 2003/035090 | 5/2003 |
| WO | 2003/092676 | 11/2003 |
| WO | 2004/026256 | 1/2004 |
| WO | 2004/026283 | 4/2004 |
| WO | 2004/037259 | 5/2004 |
| WO | 2005/046727 | 5/2005 |
| WO | 2005/053587 | 6/2005 |
| WO | 2005/102286 | 11/2005 |
| WO | 2006/002884 | 1/2006 |
| WO | 2007/150074 | 12/2007 |
| WO | 2007/150075 | 12/2007 |
| WO | 2008/023261 | 2/2008 |
| WO | 2009/023672 | 2/2009 |
| WO | 2009/114648 | 9/2009 |
| WO | 2010/019279 | 2/2010 |
| WO | 2010/078486 | 7/2010 |
| WO | 2010141505 | 12/2010 |
| WO | 2012/131463 | 10/2012 |
| WO | 2013/171146 | 11/2013 |

OTHER PUBLICATIONS

Ansel, Howard C., et al., Pharmaceutical Dosage Forms and Drug Delivery Systems, 7th Edition, 1999, pp. 1-2, 23-163, 179-243, 397-449, 552-562, Lippincott Williams & Wilkins, United States.

Apicella, A., "Poly(ethylene oxide)(PEO) and Different Molecular Weight PEO Blends Monolithic Devices for Drug Release," Biomaterials, vol. 14, No. 2, 1993, pp. 83-90.

Apicella, et al., "Poly(ethylene oxide)-Based Delivery Systems," Polymeric Drugs and Drug Administration, ACS Symposium Series 545, Chapter 9 (1994), pp. 111-125.

Apicella, et al. "Poly(ethylene oxide)(PEO) Constant Release Monolithic Devices," Polymers in Medicine: Biomedical and Pharmaceutical Applications, Chapter 3 (1992), pp. 23-37.

Aulton Michael E., et al., Pharmaceutics, The Science of Dosage Form Design, Reprinted 2000, pp. 1-2, 17-37, 62-80, 131-211, 304-321, 359-380, 550-677, Churchill Livingston, China.

Bettini, et al., "Translocation of drug particles in HPMC matrix gel layer: effect of drug solubility and influence on release rate," Journal of Controlled Release, vol. 70, No. 3, Feb. 2001, pp. 383-391.

Bhatia, R., "Effect of Molecular Mass, Concentration and Temperature on the Rheological Properties of Non-Newtonian Agueous Polymeric Solutions," 114, 2011, 202 pgs.

Chien, Yi E W., et al., "Syringeability of Nonaqueous Parenteral Formulations—Development and Evaluation of Testing Apparatus," Journal of Parenteral Science and Technology, vol. 35, No. 6, Nov. 1981, pp. 281-284.

Deighan, C.J., et al., "Rhabdomyolysis and Acute Renal Failure Resulting From Alcohol and Drug Abuse," QJ Med., vol. 93, 2000, pp. 29-33.

Dexter, M.B., et al., "The Evaluation of the Force to Expe Oily Injection Vehicles from Syringes," J. Pharm. Pharmacol., vol. 31, Aug. 1979, The Pharmaceutical Society of Great Britain, pp. 497-500.

(56) References Cited

OTHER PUBLICATIONS

Gennaro, Alfonso, Remington: The Science and Practice of Pharmacy, 20th Edition, 2000, pp. 1-3, 335-355, 654-666, 669-752, 780-820, 858-929, 995-10004, 1098-1155, 1175-1182, 1395-1399, 2037-2038, Lippincott Williams & Wilkins, Baltimore, MD, United States.

Handbook of Pharmaceutical Excipients, 1986, pp. 234-239, American Pharmaceutical Association, Washington D.C., United States.

Hardman, Joel G., et al., Goodman & Gilman's The Pharmacological Basis of Therapeutics, 9th Edition, 1996, pp. 3-27, 521-555, 557-577, McGraw-Hill, United States.

Hariharan, M., and Gupta, V.K., "A Novel Compression-Coated Tablet Dosage Form," Pharmaceutical Technology Yearbook, 2001, Jan. 1, 2001, pp. 14-19.

Hem, Stanley, et al., "Tissue Irritation Evaluation of Potential Parenteral Vehicles," Drug Development Communications, 1:5, 1974, pp. 471-477, Marcel Dekker, Inc.

Heng, Paul, et al., "Role of Surfactant on Drug Release from Tablets", Drug Development and Industrial Pharmacy, Oct. 20, 2008, pp. 951-962, Taylor & Francis, London, United Kingdom.

Huang, H., et al., "Preparation of Controlled Release Oral Dosage Forms by Low Temperature Melt Extrusion," The AAPS Journal, AAPS PharmaSci, 2000, 2(S1), 3 pgs.

Industrial and Engineering Chemistry I/EC, Golden Anniversary Year 50, Pattern for Progress, vol. 50, No. 1, Jan. 10, 1958, pp. 8-11, American Chemical Society, Easton, PA, United States.

International Search Report and Written Opinion for International Patent Application No. PCT/IB2011/003162 dated Jun. 4, 2012, 8 pgs.

International Preliminary Report on Patentability for International Patent Application No. PCT/IB2011/003162 dated Jun. 4, 2012, 14 pgs.

Kalant, H., et al., "Death in Amphetamine Users: Causes and Rates," CMA Journal, vol. 112, Feb. 8, 1975, pp. 299-304.

Kibbe, Arthur, H., "Polyethylene Oxide," Handbook of Pharmaceutical Excipients, Third Edition, 2000, pp. 399-400, PhP Pharmaceutical Press, London, United Kingdom.

Kim, C., "Drug Release from Compressed Hydrophilic POLYOX-WSR Tablets," Journal of Pharmaceutical Sciences, vol. 84, No. 3, Mar. 1995, pp. 303-306.

Maggi, L., et al, "Dissolution Behaviour of Hydrophilic Matrix Tablets Containing Two Different Polyethylene Oxides (PEOs) for the Controlled Release of a Water-Soluble Drug," Biomaterials, vol. 23, pp. 1113-1119 (2002).

Medical Economics Company, Inc., The 1997 Physician's Desk Reference ("PDR") entry for Oxycontin®, $51^{st}$ edition, Nov. 1996, Montvale, NJ pp. 2163-2164.

Meier, Barry, "U.S. Asks Painkiller Maker to Help Curb Wide Abuse," The New York Times, May 1, 2001, 3 pgs.

Modern Pharmaceutics, 3rd Edition, Drugs and the Pharmaceutical Sciences, vol. 72, 1996, pp. 21-73, 75-119, 121-153, 155-178, 333-394, 441-487, 575-609, 727-772, Marcel Dekker, Inc., United States.

Moroni, et al., "Application of Poly(oxyethylene) Homopolymers in Sustained Release Solid Formulation," Drug Dev. And Indus. Pharmacy, 21(12), pp. 1411-1428 (1995).

Philip, George, et al., "The Human Nasal Response to Capsaicin," J. Allergy Clin. Immonul., vol. 94, No. 6, Part 1, Dec. 1994, pp. 1035-1045, Mosy-Year Book, Inc., Baltimore, MD, United States.

Poynton, Charles, Digital Video and HDTV Algorithms and Interfaces, The CIE System of Colorimetry, 2003, pp. 228-229, Morgan Kaufmann Publishers, San Francisco, United States.

Prescribing Information for Concerta Extended-Release Tablets, Nov. 2010, pp. 1-9 , Ortho-McNeil-Janssen Pharmaceuticals, Inc., Titusville, United States.

Product webpage for EUDRAGIT RS 30 D [online] (Apr. 30, 2010), retrieved from the internet on (Dec. 10, 2014) from URL, http://web.archive.org/web/20100430062425/http://eudragit.evonik.com/prouct/eudragit/en/products-services/eudragit-products/sustained-release-formulations/rs-30-d/pp./default.aspx>.

Sarkar, N., "Kinetics of thermal gelation of methylcellulose and hydroxypropylmethylcellulose in aqueous solutions," Carbohydrate Polymers, vol. 26, No. 3, Jan. 1995, pp. 195-203.

Sarkar, N., "Thermal Gelation Properties of Methyl and Hydroxypropyl Methylcellulose," Journal of Polymer Science, vol. 24, No. 4, Aug. 1979, pp. 1073-1087.

Stafford, J.W., et al., "Temperature dependence of the disintegration times of compressed tablets containing hydroxypropylcellulose as binder," Journal of Pharmacy and Pharmacology, vol. 30, No. 1, Sep. 1978, pp. 1-5, John Wiley & Sons, New York, United States.

The 1997 Physician's Desk Reference ("PDR"), $51^{st}$ edition, Nov. 1996, pp. 955-957, 988-989, 2163-2167, 2366-2367, Medical Economics Company, Inc., Montvale, NJ, United States.

The Merck Index, $14^{th}$Edition, Entry Nos. 4785, 4803, 6276 and 9566, Whitehouse Station, New Jersey, USA, 2006.

Tough, Paul, "The Alchemy of Oxycontin: From Pain Relief to Drug Addiction," The New York Times, Jul. 29, 2001, 14 pgs.

U.S. Pharmacopeia & National Formulary 24/19, The Standard of Quality, United States Pharmacopeial Convention, Inc., 1999, pp. 1233-1238, 1372-1375, 1941-1951, 2002-2003, 2442-2443, 2493-2498, National Publishing, Philadelphia, PA, United States.

U.S. Pharmacopeia, p. 2206, 1995.

Vicodin®, Physican Desk Reference, 1997, pp. 1404-1405, $51^{st}$Edition, Medical Economics Company, Inc., Montvale, United States.

Wilkins, Jeffrey, N., "Pharmacotherapy of Schizophrenia Patients with Comorbid Substance Abuse," Schizophrenia Bulletin, vol. 23, No. 2, 1997, pp. 215-228.

Woodburn, K.R., et al., "Vascular Complications of Injecting Drug Misuse," British Journal of Surgery, 1996, Vo. 83, p. 1329-1334.

Yang, et al., "Characterization of Compressibility and Compactibility of Poly(ethylene oxide) Polymers for Modified Release Application by Compaction Simulator," Journal of Pharmaceutical Sciences, vol. 85, No. 10, Oct. 1996, pp. 1085-1090.

Zhang, Feng, Dissertation: "Hot-Melt Extrusion as a Novel Technology to Prepare Sustained-Release Dosage Forms," The University of Texas at Austin, pp. v-xxv, 1-260, Dec. 1999, UMI Microform 9959618, Bell & Howell Information and Learning Company, Ann Arbor, MI, United States.

Zhang, F., et al., "Properties of Sustained-Release Tablets Prepared by Hot-Melt Extrusion," Pharmaceutical Development and Technology, vol. 4, No. 2, pp. 241-250 (1999).

* cited by examiner

TAMPER RESISTANT SOLID ORAL DOSAGE FORMS

CROSS REFERENCE TO RELATED APPLICATION(S)

This application is a continuation of U.S. patent application Ser. No. 14/992,789 filed on Jan. 11, 2016, which is a division of U.S. patent application Ser. No. 13/997,560 filed on Sep. 23, 2013, which is a national stage entry of PCT Application No. PCT/IB2011/003162 filed on Dec. 22, 2011, which claims the benefit of U.S. Provisional Application No. 61/426,903 filed on Dec. 23, 2010, the disclosures of which are hereby incorporated by reference herein in their entireties.

FIELD OF THE INVENTION

The present invention relates to the field of solid oral pharmaceutical dosage forms that are resistant to tampering such as splitting, crushing, shearing, grinding or chewing.

BACKGROUND

Solid oral pharmaceutical dosage forms, most often in the form of tablets, are a common mode of delivering active agents for the treatment or prevention of diseases and conditions. For a variety of reasons, patients who are prescribed these dosage forms sometimes attempt to split or divide the formulation into multiple units. These reasons include cost containment, as the price of a specified amount of a dosage form in a given strength is often less than double the price (or the same price) as compared to the same amount of dosage forms in half the strength. This provides the incentive for a patient to split their dose under their own initiative, or under the direction of their health care provider. There have also been proposals for mandatory tablet splitting by various state Medicaid programs.

Tablet splitting can be problematic if the patient has cognitive impairment that limits the ability of the patient to understand and remember instructions for tablet splitting; or arthritis or other impairment of manual dexterity; or Parkinson's disease or other tremors; or visual impairment.

Another problem with tablet splitting is overdosing or underdosing as it is often difficult to split tablets with a degree of certainty as to the dose contained in each fragment. This can be a particular issue with respect to active agents with a narrow therapeutic window (e.g., warfarin, levothyroxine and digoxin), where a slight variation in dosing can lead to sub-therapeutic or toxic plasma levels.

Further, the splitting of certain controlled release dosage forms (e.g., opioids, theophylline, calcium channel blockers) compromises the integrity of the dosage form, resulting in the immediate release of an amount of active agent intended for release over an extended period of time. This can also result in toxic plasma levels.

A study of 11 commonly split tablets showed that 8 of the 11 tablets, when split, failed to produce half-tablets that met the content uniformity test for tablets from the United States Pharmacopeia, which requires a discrepancy that falls within 85% and 115% of the intended dosage. Notably, scoring of the tablet did not predict whether the tablet would pass or fail this test. See, Teng et al. Lack of medication dose uniformity in commonly split tablets. *J Am Pharm Assoc.* 2002; 42:195-9.

Splitting or crushing of dosage forms of drugs susceptible to abuse (e.g., opioid analgesics) is also a common method of abusers to obtain an amount of active agent for illicit use. For example, immediate release opioid formulations can be split or crushed in order to provide the active agent available for parenteral or nasal abuse.

Controlled release opioid formulations can also be split or crushed in order to make the active agent available therein (intended for release over an extended period) available for immediate parenteral, nasal or oral administration.

There is a need in the art for both immediate and controlled release solid oral dosage forms that are resistant to tampering (e.g., splitting or crushing) which minimize the problems associated therewith.

All references disclosed herein are incorporated by reference in their entireties for all purposes.

SUMMARY OF THE INVENTION

It is an object of certain embodiments of the present invention to provide a solid oral dosage form comprising an active agent (e.g., an opioid analgesic), which is resistant to tampering (e.g., splitting, crushing, shearing, grinding, chewing or a combination thereof).

It is an object of certain embodiments of the present invention to provide a solid oral dosage form comprising an active agent, which is subject to less overdosing caused by splitting the dosage form into uneven doses.

It is an object of certain embodiments of the present invention to provide a solid oral dosage form comprising an active agent, which is subject to less underdosing caused by splitting the dosage form into uneven doses.

It is an object of certain embodiments of the present invention to provide a solid oral dosage form comprising an active agent susceptible to abuse (e.g., an opioid analgesic), which is subject to less parenteral abuse than other dosage forms.

It is an object of certain embodiments of the present invention to provide a solid oral dosage form comprising an active agent susceptible to abuse, which is subject to less intranasal abuse than other dosage forms.

It is an object of certain embodiments of the present invention to provide a solid oral dosage form comprising an active agent susceptible to abuse, which is subject to less oral abuse than other dosage forms.

It is an object of certain embodiments of the present invention to provide a solid oral dosage form comprising an active agent susceptible to abuse, which is subject to less diversion than other dosage forms.

It is a further object of certain embodiments of the present invention to provide a method of treating pain in human patients with a solid oral dosage form comprising an opioid analgesic while reducing the abuse potential of the dosage form.

It is a further object of certain embodiments of the present invention to treat a disease or condition (e.g., pain) by administering a solid oral dosage form as disclosed herein to a patient in need thereof.

It is a further object of certain embodiments of the present invention to provide a method of manufacturing an oral dosage form of an active agent (e.g., an opioid analgesic) as disclosed herein.

It is a further object of certain embodiments of the present invention to provide a use of a medicament in the manufacture of a dosage form as disclosed herein that is resistant to tampering (e.g., splitting, crushing, shearing, grinding, chewing or a combination thereof).

It is a further object of certain embodiments of the present invention to provide a use of a medicament (e.g., an opioid analgesic) in the manufacture of a dosage form as disclosed herein for the treatment of a disease state (e.g., pain).

These objects and others are accomplished by the present invention, which in certain embodiments is directed to a solid oral dosage form comprising (a) an inert tamper resistant core; and (b) a coating surrounding the core, the coating comprising an active agent.

In certain embodiments, the present invention is directed to a method of preparing a solid oral dosage form comprising: surrounding an inert tamper resistant core with a coating comprising an active agent.

In certain embodiments, the present invention is directed to a method of preparing a solid oral dosage form comprising: (a) preparing an inert tamper resistant core; and (b) surrounding the core with a coating comprising an active agent.

In certain embodiments, the present invention is directed to a method of treating a subject or patient for a disease or condition comprising administering to a subject or patient in need thereof a solid oral dosage form as disclosed herein. The methods of treating a disease or condition include single or repeated dosing over a time interval.

In certain embodiments, the present invention is directed to a method of providing preventative treatment to a subject or patient comprising administering to a subject or patient in need thereof a solid oral dosage form as disclosed herein. The preventative methods include single or repeated dosing over a time interval.

In certain embodiments, the present invention is directed to a method of treating pain comprising administering to a patient in need thereof, a solid oral dosage form comprising an opioid analgesic as disclosed herein.

In certain embodiments, the present invention is directed to a method of reducing the incidence of overdosing, comprising dispensing a solid oral dosage form as disclosed herein.

In certain embodiments, the present invention is directed to a method of reducing the incidence of underdosing, comprising dispensing a solid oral dosage form as disclosed herein.

In certain embodiments, the present invention is directed to a method of reducing the abuse potential of an active agent susceptible to abuse comprising dispensing a solid oral dosage form as disclosed herein.

In certain embodiments, the present invention is directed to method of reducing the incidence of overdosing, comprising preparing a solid oral dosage form as disclosed herein.

In certain embodiments, the present invention is directed to method of reducing the incidence of underdosing, comprising preparing a solid oral dosage form as disclosed herein.

In certain embodiments, the present invention is directed to a method of reducing the abuse potential of an active agent susceptible to abuse comprising preparing a solid oral dosage form as disclosed herein.

In certain embodiments, the present invention is directed to a use of a drug in the preparation of a tamper resistant solid oral dosage form for treating or preventing a disease, the dosage form comprising: (a) an inert tamper resistant core; and (b) a coating surrounding the core, the coating comprising an active agent.

In certain embodiments, the present invention is directed to a use of a drug susceptible to abuse in the preparation of a tamper resistant solid oral dosage form, the dosage form comprising: (a) an inert tamper resistant core; and (b) a coating surrounding the core, the coating comprising an active agent.

The term "inert" with respect to an inert core means that an active agent is not included in the core. This does not include a minimal amount of active agent that may migrate into the core from the coating during the manufacturing process or during storage. The term "inert" also does not exclude aversive agents such as opioid antagonists in the core of the present invention.

The term "sustained release" is defined for purposes of the present invention as the release of the drug at such a rate that blood (e.g., plasma) concentrations are maintained within the therapeutic range but below toxic concentrations over a period of time of at least about 12 hours or longer, or at least 24 hours or longer. Preferably, a controlled release dosage form can provide once daily or twice daily dosing.

The term "controlled-release" encompasses "sustained release", "extended release", "delayed release" or any other modified (i.e., non-immediate) release.

The term "polyethylene oxide" is defined for purposes of the present invention as a composition of polyethylene oxide having a molecular weight of at least 25,000, based on rheological measurements, and preferably having a molecular weight of at least 100,000. Compositions with lower molecular weight are usually referred to as polyethylene glycols.

For purposes of the present invention, the term "opioid analgesic" means one or more compounds selected from base opioid agonists, mixed opioid agonist-antagonists, partial opioid agonists, pharmaceutically acceptable salts, complexes, stereoisomers, ethers, esters, hydrates and solvates thereof and mixtures thereof.

The term "patient" means a subject who has presented a clinical manifestation of a particular symptom or symptoms suggesting the need for treatment, who is treated preventatively or prophylactically for a condition, or who has been diagnosed with a condition to be treated.

The term "subject" is inclusive of the definition of the term "patient" and does not exclude individuals who are entirely normal in all respects or with respect to a particular condition.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

As used herein, resistance to splitting, crushing, shearing, grinding and/or chewing results from a dosage form (or any portion thereof) having a preferable breaking strength of at least 400 Newtons.

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of enantiomers.

The term "resolution" refers to the separation or concentration or depletion of one of the two enantiomeric forms of a molecule.

DETAILED DESCRIPTION

In some instances, for particular medications, tablet splitting is condoned or even encouraged by physicians as a means of reducing the high cost of prescription drugs. Widespread use of tablet splitting, however, without consideration of the patient and the particular dosage form can have detrimental effect.

Potential detrimental effects include (i) an increased amount of drug released over a short period of time associated with splitting certain controlled release dosage forms (e.g., controlled release opioids); (ii) an upset stomach or foul taste in a patient's mouth with splitting dosage forms of foul tasting or gastro-irritative agents (e.g., ciprofloxacin, aspirin); (iii) unusable fragments with the attempted splitting of friable dosage forms such as sublingual nitroglycerin; and (iv) uneven dosing with more drug in one half than in the other, which is a particular problem with drugs tablet which require a narrow therapeutic window for each individual patient (e.g., levothyroxine, warfarin and digoxin).

Splitting and crushing is also a methodology utilized by drug abusers in order to liberate active agent from a dosage form for illicit use (e.g., parenteral, nasal or oral abuse). This is a problem with both immediate release and controlled release dosage forms containing drugs susceptible to abuse (e.g., opioid analgesics or stimulants).

The present invention thus provides a solid oral dosage form that is resistant to tampering (e.g., splitting, crushing, shearing, grinding, chewing or a combination thereof) that might otherwise be carried out in order to liberate the active agent contained therein, thus reducing the likelihood of these associated detrimental effects.

Figure 1:
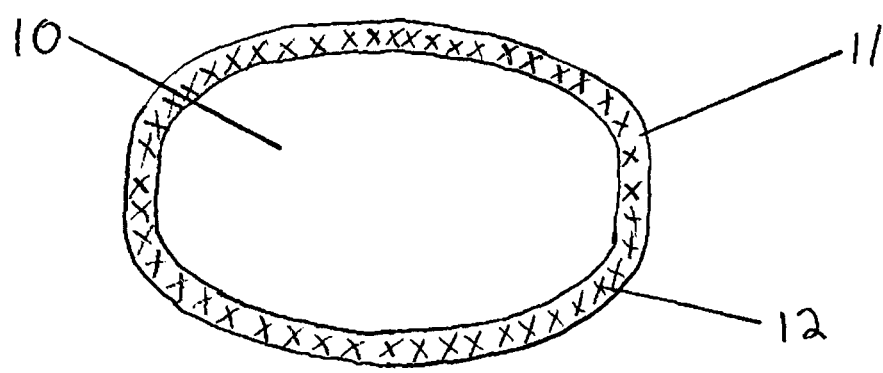
FIG. 1 is a graphical representation of a single coated core embodiment of the present invention.

Referring to FIG. 1, the dosage forms of the present invention may comprise an inert (i.e., without an active agent) tamper resistant core (10); and a coating surrounding the core (11), the coating comprising an active agent (12).

Figure 2:
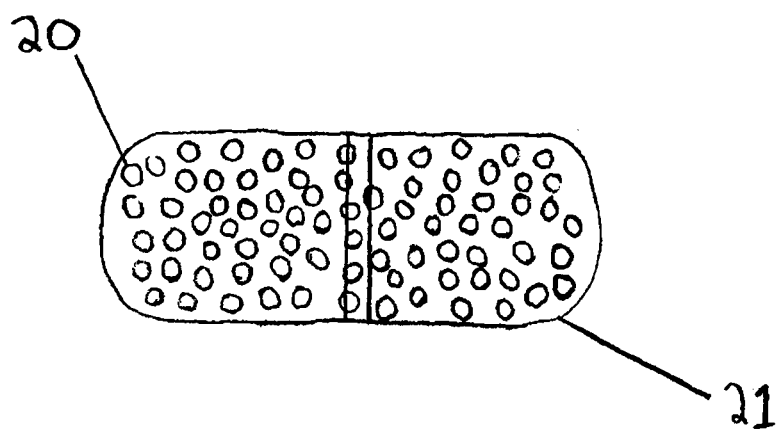
FIG. 2 is a graphical representation of a multiparticulate embodiment of the present invention.

The dosage form can be a single coated core (e.g., in tablet form) which coating contains the entire intended dose as depicted in FIG. 1 or can be in the form of multiparticulates as depicted in FIG. 2, with a plurality of tamper resistant coated cores (20). The tamper resistant coated cores have an active agent coating surrounding each core, with the active agent divided among the plurality of coated cores. The multiparticulates can be contained in an optional pharmaceutically acceptable capsule (21).

Figure 3:
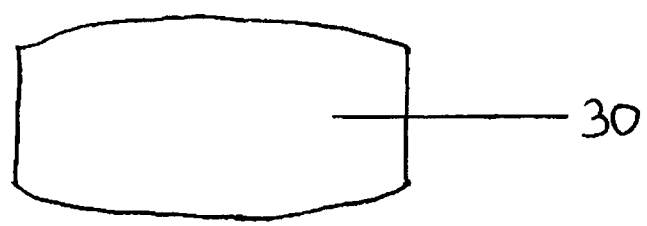
FIG. 3 is a graphical representation of a unitary core of the present invention.
Figure 4:
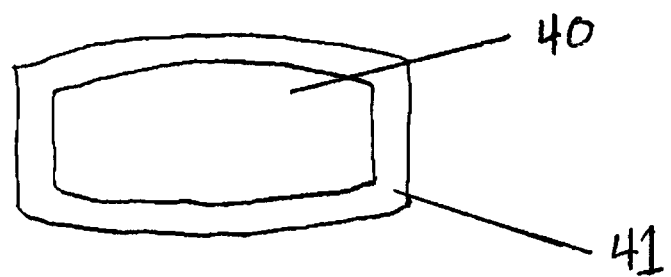
FIG. 4 is a graphical representation of a core of the present invention having an inner component and an outer component.

As depicted in FIG. 3, the inert tamper resistant core can be unitary (30) with a sufficient hardness in order to be tamper resistant or as depicted in FIG. 4, can have an inner component (40) which is tamper or non-tamper resistant, that is coated with a tamper resistant outer component (41) of a suitable hardness.

The coating on the inert tamper resistant cores can have a suitable amount of active agent to provide a therapeutic effect. Depending on the active agent, the amount can be, e.g., from about 0.1 mg to about 1 gram, about 1 mg to about 500 mg, or about 10 mg to about 100 mg. Typically, the weight of the coating when applied to the inert cores is about 1% to about 25% of the total weight of the dosage form although this can be higher or lower depending on the load of active agent required for a therapeutic effect.

The tamper resistant cores of the present invention are of a sufficient hardness to present difficulty in splitting, crushing, shearing, grinding or chewing the final dosage form in an attempt to fragment the dosage form. Preferably, the tamper resistant core has a breaking strength of at least about 400 Newtons, at least about 500 Newtons, at least about 600 Newtons, at least about 700 Newtons, at least about 800 Newtons or at least about 1 KiloNewton.

The present invention further provides a pharmaceutical package comprising a single or plurality of solid oral dosage forms, e.g., tablets, of the present invention. The package can be, e.g., a blister pack, bottle, tube, bags, vial, box, container or any other suitable packaging material. The container can hold an amount of dosage forms such as 1 to 5000, 1 to 1000, 1 to 500, 1 to 120, 1 to 100, 1 to 90, 1 to 60, 1 to 50, 1 to 30, 1 to 28, 1 to 21, 1 to 14, 1 to 7 or 1 to 5. Specific amounts of dosage forms included in packaging materials include 1 (single dose), 7 (e.g., once daily dosing for one week), 14 (e.g., twice daily dosing for one week), 21 (e.g., three times daily dosing for 1 week), 28 (e.g., four times daily dosing for 1 week), 30 (e.g., once daily dosing for one month), 60 (e.g., twice daily dosing for one month), 90 (e.g., three times daily dosing for 1 month), 100 (typically a 1-3 month supply) or 120 (e.g., four times daily dosing for 1 month).

Immediate Release Dosage Forms

The solid oral dosage forms of the present invention can be in the form of an inert tamper resistant core coated with an immediate release coating of the active agent. Immediate release dosage forms of drugs susceptible to abuse are sometimes split or crushed in order for the drug to be readily available for parenteral or nasal abuse. Thus, the present invention may discourage the illicit use of immediate release formulations by inhibiting the ability to effectively split or crush the dosage form. The immediate release tamper resistant dosage forms of the present invention also discourage the splitting of dosage forms that can result in an overdose or underdose of the active agent contained therein.

The immediate release coating can be applied by various methodologies such as spray coating, dipping, powder layering or compression coating. In embodiments wherein the active agent does not provide the necessary bulk to process the immediate release coating, various excipients can be utilized in order to facilitate processing.

In spray coated dosage forms, the active agent is typically dissolved in solution and sprayed onto the inert cores of the present invention in either single or multiparticulate form. The process may include spraying of very finely atomized droplets of solution onto the inert cores in a stream of hot process air or other suitable gas. By having the drug in solution rather than suspension, improved uniformity of the coating can be achieved. The solution can be an aqueous or organic solvent and include various binders such as polyvinylpyrrolidone, natural and synthetic gums including gum arabic, hydroxypropylmethylcellulose, hydroxypropylcellulose, carboxymethylcellulose, methylcellulose, pullulan, dextrin, starch, polyvinyl alcohol among others.

In powder layering, inert tamper resistant cores of the present invention may be spray coated with a binder to provide tackiness. The active agent in powder form is then sprayed onto the binder coated inert cores. The spraying powder comprising the active agent may also include additional excipients, including glidants, diluents, stabilizers, coloring agents, and additional binders. Suitable glidants include, e.g., colloidal silicon dioxide and/or talc. Suitable diluents include, e.g., polysaccharides, monosaccharides, corn starch, and the like.

In compression coating, the active agent is combined with suitable excipients (e.g., glidants, diluents) and compression coated onto the inert tamper resistant cores of the present invention. In certain embodiments, a Manesty Dry-Cota press (e.g., Model 900) can be utilized. This apparatus consists of two side by side interconnected tablet presses where the inert core is made on one press and then mechanically transferred to the next press for compression coating. Each press has an independent powder feed mechanism so that the inert core blend is loaded on one machine, and the coating blend is loaded on the other machine. Mechanical transfer arms rotate between the machines to remove cores from the core press and transfer them to the coating press. Other presses which may be used to prepare the dosage forms of the present invention include Elizabeth Hata HT-AP44-MSU-C; Killian RLUD; and Fette PT 4090, each of which has a dual feed system for coating blend and pre-made cores.

In any of the above immediate release coating embodiments, a film coat (e.g., for taste, protective or cosmetic purposes) can be overcoated on the immediate release layer and/or utilized as an undercoat between the inert core and the active agent layer. An example of such a coating is Opadry®.

Controlled Release Dosage Forms

The solid oral dosage forms of the present invention can be in the form of an inert tamper resistant core coated with a controlled release coating of the active agent. Splitting controlled release dosage forms is subject to the same issues as immediate release dosage forms (e.g., parenteral and nasal abuse, non-uniform fragments). In addition, controlled release dosage forms are subject to oral abuse when an amount of drug intended for an extended period of time is liberated for immediate illicit use by splitting or crushing. Thus, the dosage forms of the present invention discourage the illicit use of controlled release formulations. Further, if a patient administers a half tablet of many controlled release dosage forms (without illicit intent), often the integrity of the dosage form is compromised and a toxic amount of active agent can be released. The controlled release tamper resistant dosage forms of the present invention also discourage the splitting of dosage forms that can result in an overdose or underdose of the active agent contained therein.

In certain embodiments, an immediate release coating of the active agent is applied to the inert tamper resistant cores of the present invention (e.g., as disclosed above) followed by an application of a controlled release coating over the active layer. In other embodiments, the active agent can be included (i.e., dispersed) in controlled release excipients in the coating without a separate active agent layer and controlled release layer. The controlled release coating can be applied by various methodologies (e.g., spray coating and compression coating as discussed above) with the inclusion of excipient(s) to provide the desired release rate.

A non-limiting list of suitable controlled release materials which may be selected for inclusion in the controlled release layer according to the present invention includes hydrophilic and hydrophobic materials such as sustained release polymers, gums, acrylic resins, protein-derived materials, waxes, shellacs, and solid or semi-solid oils such as hydrogenated castor oil and hydrogenated vegetable oil. More specifically, the controlled release materials can be, e.g., alkylcelluloses such as ethylcellulose, acrylic and methacrylic acid polymers and copolymers, and cellulose ethers, such as hydroxyalkylcelluloses (e.g., hydroxypropylmethylcellulose) and carboxyalkylcelluloses. Waxes include, e.g., natural and synthetic waxes, fatty acids, fatty alcohols, and mixtures of the same (e.g., beeswax, carnauba wax, stearic acid and stearyl alcohol). Certain embodiments utilize mixtures of two or more of the foregoing controlled release materials in the matrix of the core. However, any pharmaceutically acceptable hydrophobic or hydrophilic controlled release material which is capable of imparting controlled release of the active agent may be used in accordance with the present invention. The controlled release coating may also contain suitable quantities of additional excipients, e.g., lubricants, binders, granulating aids, diluents, colorants, flavorants and glidants, all of which are conventional in the pharmaceutical art.

In any of the controlled release coating embodiments, a film coat (e.g., for taste, protective or cosmetic purposes) can be overcoated on the controlled release layer and/or utilized as an undercoat between the inert core and the active agent layer.

Other Tamper Resistant Embodiments

In other embodiments, the inert tamper resistant dosage forms that are resistant to splitting, crushing, etc., can further include additional agents that are aversive to oral, parenteral and/or nasal abuse of the dosage form.

In certain embodiments of the present invention, the dosage form comprises a bittering agent in the inert core, in the coating, or in both the inert core and the coating, to discourage an abuser from tampering with the dosage form (e.g., by chewing, splitting or crushing) and thereafter inhaling or swallowing the tampered dosage form due to the resultant unpleasant taste. Various bittering agents can be employed including, for example and without limitation, natural, artificial and synthetic flavor oils and flavoring aromatics and/or oils, oleoresins and extracts derived from plants, leaves, flowers, fruits, etc., and combinations thereof. Nonlimiting representative flavor oils include spearmint oil, peppermint oil, *eucalyptus* oil, oil of nutmeg, allspice, mace, oil of bitter almonds, menthol and the like. Useful bittering agents can be artificial, natural and synthetic fruit flavors such as citrus oils including lemon, orange, lime, grapefruit, and fruit essences and the like. Additional bittering agents include sucrose derivatives (e.g., sucrose octaacetate), chlorosucrose derivatives, quinine sulphate, and the like. The preferred bittering agent for use in the present invention is Denatonium Benzoate NF-Anhydrous, sold under the name Bitrex®. (Macfarlan Smith Limited, Edinburgh, UK).

In certain embodiments of the present invention, the dosage form comprises an irritant in the inert core, in the coating, or in both the inert core and the coating, to discourage an abuser from tampering with the dosage form (e.g., by chewing, splitting or crushing) and thereafter inhaling or swallowing the tampered dosage form due to the resultant burning or irritating effect to the abuser upon inhalation, injection, and/or swallowing of the tampered dosage form. Various irritants can be employed including, for example and without limitation capsaicin, a capsaicin analog with similar type properties as capsaicin, and the like. Some capsaicin analogues or derivatives include for example and without limitation, resiniferatoxin, tinyatoxin, heptanoylisobutylamide, heptanoyl guaiacylamide, other isobutylamides or guaiacylamides, dihydrocapsaicin, homovanillyl octylester, nonanoyl vanillylamide, or other compounds of the class known as vanilloids.

In other embodiments, a gelling agent can be included in the inert core, in the coating, or in both the inert core and the coating, such that when the dosage form is tampered with, the gelling agent preferably imparts a gel-like quality to the tampered dosage form in the presence of a liquid (e.g., an extracting solvent or within the mucosa) to hinder the ability to inject or inhale the active agent. Various gelling agents can be employed including, for example and without limitation, sugars or sugar derived alcohols, such as mannitol, sorbitol, and the like, starch and starch derivatives, cellulose derivatives, such as microcrystalline cellulose, sodium caboxymethyl cellulose, methylcellulose, ethyl cellulose, hydroxyethyl cellulose, hydroxypropyl cellulose, and hydroxypropyl methylcellulose, attapulgites, bentonites, dextrins, alginates, carrageenan, gum tragacanth, gum acacia, guar gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof.

In other embodiments, opioid antagonists can be used in the present invention to discourage illicit use. The antagonist can be naltrexone, naloxone, nalmefene, nalide, nalmexone, nalorphine, nalorphine dinicotinate, cyclazocine, levallorphan, pharmaceutically acceptable salts thereof, and mixtures thereof. The antagonist can be in the coating, the inert core, or in both the inert core and the coating. The antagonist (as well as the other aversive agents) can be releasable or sequestered, such that the agent is only releasable if the dosage form is tampered with. Sequestered dosage forms can be formulated in accordance with U.S. Pat. No. 6,696,088.

Inert Tamper Resistant Cores

Non-limiting examples of suitable inert core materials include polymers such as polyalkylene oxides (e.g., polymethylene oxides, polyethylene oxides, polypropylene oxides) polyethylenes, polypropylenes, polyvinyl chlorides, polycarbonates, polystyrenes, polyacrylates, polycaprolactone, polymethacrylates copolymers thereof, and mixtures thereof.

A suitable inert core material can be processed to produce a tamper resistant core by heating the material (i.e., curing) to its melting (softening) point and then cooling the material. The heating may be monitored by a temperature measurement in the interior of a formed core using a temperature sensor. In other embodiments, the core can be subject to ultrasonic forces. Compressive force may optionally be applied, continuously or discontinuously, to form the core. The method of producing a tamper resistant core according to the invention may be accelerated by rapidly cooling formed cores after the application of heat. This may proceed, for example by conveying the formed cores through a cooling chamber or by placing them into a cooling medium, such as for example into a liquid gas. See, U.S. Patent Publication No. 2007/0003616.

In an aspect of the invention, a core is formed having a breaking strength of at least 400 Newtons. In another aspect of the invention, a core is formed having a breaking strength of at least 500 Newtons, at least 600 Newtons, at least 700 Newtons, at least 800 Newtons or at least 1 KiloNewton.

Cores of such breaking strength can be prepared by adapting the technologies described in the art to the presently disclosed invention. Non-limiting examples of such technologies are described in the following published US patent applications: US 2005/0236741 and US 2008/0317854, which describe abuse-proof dosage forms that incorporate a binder having a breaking strength of 500 Newtons, and exposing the dosage forms to ultrasound and force; US 2006/0002859 and US 2008/0312264, which describe abuse-proof dosage forms having a breaking strength of 500 Newtons, produced by melt extrusion with a planetary-gear extruder; US 2006/0188447, US 2008/0311049, US 2009/0005408 and US 2007/0003616, which describe abuse-proof dosage having a polymer with a breaking strength of at least 500 Newtons; US 2006/0193782 and US 2008/0247959 which describe abuse-proof dosage forms having a polymer with a breaking strength of at least 500 Newtons and thermoformed without extrusion; US 2006/0193914, US 2008/0311187, and US 2010/0151028 which describe crush resistant dosage forms having a resistance to crushing of at least 400 Newtons and release of active agent that is at least partially delayed.

In order to achieve a core breaking strength according to the invention, the core can comprise at least one natural or synthetic wax with the specified breaking strength. Waxes with a softening point of at least 60° C. are preferably used, for example, carnauba wax and beeswax. The wax can be used together with one or more suitable core polymers.

A tamper resistant core according to the invention can also be formed by coating a conventional core with a tamper resistant material such as cellulose acetate, such that the core is thereby rendered tamper resistant. The tamper resistant material may be coated onto a core using coating methods described above. The active agent coating (immediate or controlled release) can then be coated onto the tamper resistant coating of the inert core.

Splitting a dosage form can be more difficult when it has an asymmetrical shape. Splitting may also be more difficult if the dosage form has a shape that is roundish or spherical as compared to flattish, oval or longish.

Shaping of the tablet may be performed by applying force, e.g., a force of greater than or equal to 0.5 KiloNewton, preferably of 1 to 100 KiloNewton. The force is preferably exerted with the assistance of a press, preferably a tablet press, with shaping rollers or shaping belts equipped with rollers. The formulation mixture may also be extruded with the assistance of an extruder to yield a strand which is singulated into formed articles having the desired size.

A suitable method for determining the breaking strength of a tablet core is published in the European Pharmacopoeia 1997, page 143, 144, method no. 2.9.8.

In other embodiments, the inert core material can include a natural or synthetic abrasive material such as metal oxides (e.g., alumina, ceria, silica, and zirconia), carbides (e.g., calcium carbide, silicon carbide (carborundum), tungsten carbide and cementite), nitrides (e.g., titanium nitride, aluminum nitride and gallium nitride) and co-formed products or combinations thereof. The abrasive material is preferably durable enough to inhibit splitting, crushing, shearing, grinding, or chewing of the dosage form, while also not presenting a safety/toxicity issue to the patient.

Active Agents

A solid oral dosage form of the present invention may include any drug, or combination of drugs, that can be incorporated into a coating for application directly over an inert tamper resistant core. The present invention is particularly suited to drugs that should not be administered in split or divided solid dosage forms. Accordingly, the present invention is particularly suited to drugs such as, for example, antibiotics, opioids, hormones, anti-psychotic agents, stimulants, anti-hypertensive agents, and sedatives. More specific, non-limiting examples include controlled release verapamil, extended-release oxycodone, extended release morphine, coated aspirin, niroglycerin, digoxin, levothyroxine and warfarin.

The inert tamper resistant cores can be used to produce solid oral dosage forms according to the present invention that make drug abuse more difficult. A drug abuser will find it more difficult to simply split or crush a solid oral dosage form according to the present invention to produce a powder suitable for nasal or intravenous administration. Accordingly, the instant invention is particularly suited to prepare oral dosage forms of commonly abused drugs such as, for example, opioids, tranquilizers, CNS depressants, CNS stimulants, anti-anxiolytics (e.g., benzodiazepines), sedatives, hypnotics, stimulants (including amphetamine, dextroamphetamine, dinoprostone, methylphenidate, modafinil, pemoline and appetite suppressants such as phenylpropanolamine), and cannabinoids, among others.

Opioids useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts, stereoisomers, ethers, esters, hydrates, solvates, and mixtures thereof. Preferably, the opioid is selected from the group consisting of codeine, hydrocodone, hydromorphone, morphine, oxycodone, oxymorphone, tramadol, pharmaceutically acceptable salts, stereoisomers, ethers, esters, hydrates, solvates, and mixtures thereof.

In other embodiments, the active agent can be selected from barbiturates such as phenobarbital, secobarbital, pentobarbital, butabarbital, talbutal, aprobarbital, mephobarbital, butalbital, pharmaceutically acceptable salts thereof, and the like; benzodiazepines such as diazepam, chlordiazepoxide, alprazolam, triazolam, estazolam, clonazepam, flunitrazepam, pharmaceutically acceptable salts thereof, and the like; stimulants such as gamma-hydroxybutyrate, dextroamphetamine, methylphenidate, sibutramine, methylenedioxyrnethamphetamine, pharmaceutically acceptable salts thereof, and the like; other agents such as marinol, meprobamate and carisoprodol; and all pharmaceutically acceptable salts, complexes, stereoisomers, ethers, esters, hydrates, solvates, and mixtures thereof.

In other embodiments, the active agent can be an antipsychotic agent such as amisulpride, aripiprazole bifemelane, bromperidol, clozapine, chlorpromazine, haloperidol, iloperidone loperidone, olanzapine, quetiapine, fluphenazine, furnarate, risperidone, thiothixene, thioridazine, sulpride, ziprasidone, and all pharmaceutically acceptable salts, complexes, stereoisomers, ethers, esters, hydrates, solvates, and mixtures thereof.

In other embodiments, the active agent can be an antihypertensive agent such as beta adrenergic blockers (e.g., propranolol, metoprolol and timolol), calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates and pharmaceutically acceptable salts, complexes, stereoisomers, ethers, esters, hydrates, solvates, and mixtures thereof.

In further embodiments, other therapeutically active agents may be used in accordance with the present invention. Examples of such therapeutically active agents include antihistamines (e.g., dimenhydrinate, diphenhydramine, chlorpheniramine and dexchlorpheniramine maleate), non-steroidal anti-inflammatory agents (e.g., naproxen, diclofenac, indomethacin, ibuprofen, sulindac, Cox-2 inhibitors), acetaminophen, anti-emetics (e.g., metoclopramide, methylnaltrexone), anti-epileptics (e.g., phenyloin, meprobmate and nitrazepam), anti-tussive agents and expectorants, anti-asthmatics (e.g. theophylline), antacids, anti-spasmodics (e.g. atropine, scopolamine), antidiabetics (e.g., insulin), bronchodilators (e.g., albuterol), steroids (e.g., hydrocortisone, triamcinolone, prednisone), antibiotics (e.g., tetracycline, penicillins, cephalosporins, erythromycins), hormones (e.g., estrogens and progestins), anti-hemorrhoidals, psychotropics, anti-diarrheals, mucolytics, decongestants (e.g. pseudoephedrine), laxatives, vitamins, and pharmaceutically acceptable salts, complexes, stereoisomers, ethers, esters, hydrates, solvates, and mixtures thereof.

Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, dicyclohexylamine salt, N,N'-dibenzylethylenediamine salt and the like.

The tamper resistant dosage forms can be used to treat any disease or condition requiring pharmacological therapy. Such disease states include without limitation, pain and anti-psychotic disorders.

Pain syndromes include but are not limited to acute or chronic pain that is either nociceptive (for example somatic or visceral) or non-nociceptive (for example neuropathic or sympathetic) in origin. In some embodiments, the pain is nociceptive pain including, but not limited to, surgical pain, inflammatory pain such as that associated with inflammatory bowel syndrome or rheumatoid arthritis, pain associated with cancer, and pain associated with osteoarthritis. In some embodiments, the pain is non-nociceptive pain including, but not limited to, neuropathic pain such as post-herpetic neuralgia, trigeminal neuralgia, focal peripheral nerve injury, anesthesia clolorosa, central pain (for example, post-stroke pain, pain due to spinal cord injury or pain associated with multiple sclerosis), and peripheral neuropathy (for example, diabetic neuropathy, inherited neuropathy or other acquired neuropathies).

Psychotic disorder include but are not limited to psychotic depression, postpartum depression, affective disorder, schizoaffective disorder, schizophreniform disorder, schizophrenia, delusional disorder, brief psychotic disorder, shared psychotic disorder, borderline personality disorder, manic-depressive disorder, obsessive-compulsive disorder, Huntington's Disease, Tourette's syndrome and tic disorder.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

This application claims priority from U.S. Provisional Application Ser. No. 61/426,903, filed Dec. 23, 2010, the disclosure of which is hereby incorporated by reference.

EXAMPLES

The following examples are provided to illustrate, but not to limit, the present invention.

Prophetic Example 1

A tablet may be constructed using the following materials and processes:

Core

| | |
|---|---|
| Polyethylene oxide | 149 mg |
| Magnesium stearate | 1 mg |
| Total | 150 mg |

Coating

| | |
|---|---|
| Active pharmaceutical ingredient (API) | 5 mg |
| HPMC | 10 mg |

Overcoat

| | |
|---|---|
| HPMC | 10 mg |

Manufacturing Process

I. Blend the polyethylene oxide with the magnesium stearate.
II. Compress into round 7 mm tablet cores using a rotary tablet press to achieve a target weight of 150 mg.
III. Cure the cores in a conventional tablet coater by heating to an exhaust temperature of 72 C for 15 minutes.

IV. Allow the tablets to cool while continuously rotating the tablet bed. Add a dusting of magnesium stearate, if necessary, to prevent the cores agglomerating.
V. Disperse the active ingredient and HPMC for the active coating in water to a solids content of 10-15%.
VI. Apply the active ingredient-containing coating to the tablet cores using the tablet coater to a target weight gain of 15 mg/tablet.
VII. Disperse the HPMC (for the overcoat) in water to a solids content of 10-15%.
VIII. Apply the overcoat to the active ingredient-coated cores in the tablet coater to achieve a target weight gain of 10 mg/tablet.

Prophetic Example 2

I. An inert tablet was prepared using 200 mg of high molecular weight polyethylene oxide (PEO 303—MW 7,000,000), as set forth below.
II. To prepare the core, a single station Manesty Type F 3 tablet press is equipped with 7.94 mm, round, standard concave plain tooling. A powdered aliquot of the PEO, was weighed out to target weight of 200 mg, charged into the die, and compressed to form the inert.
III. Several compression inert tablets prepared as above are placed onto a tray, which are placed in a Hotpack model 435304 oven targeting 72° C. for 30 minutes to cure.
IV. Thereafter, 20 mg of hydrocodone bitartrate are spray coated onto the inert core in a hydroxypropylmethycellulose solution.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

The invention claimed is:

1. A solid oral dosage form comprising:
    (a) an inert tamper resistant core having a breaking strength of at least 400 Newtons, wherein the inert tamper resistant core comprises an inner component and an outer component coated on the inner component; and
    (b) a coating surrounding the inert tamper resistant core, wherein the coating comprises an opioid analgesic dispersed in a controlled release material,
    wherein the opioid analgesic is selected from the group consisting of morphine, codeine, oxycodone, hydrocodone, hydromorphone, oxymorphone, and pharmaceutically acceptable salts thereof, wherein the coating provides a controlled release of the opioid analgesic for a time of at least 12 hours,
    wherein the inert tamper resistant core does not include the opioid analgesic,
    wherein the solid oral dosage form is a tablet comprising a single coated core that comprises a therapeutically effective amount of the opioid analgesic.

2. The solid oral dosage form of claim 1, wherein the tamper resistant core comprises a gelling agent.

3. The solid oral dosage form of claim 2, wherein the gelling agent is selected from the group consisting of sugar, sugar derived alcohols, mannitol, sorbitol, starch, microcrystalline cellulose, sodium carboxymethylcellulose, methylcellulose, ethylcellulose, hydroxyethylcellulose, hydroxypropylcellulose, hydroxypropyl methylcellulose, attapulgite, bentonite, dextrin, alginate, carrageenan, gum tragacanth, gum acacia, guar gum, xanthan gum, pectin, gelatin, kaolin, lecithin, magnesium aluminum silicate, carbomer, carbopol, polyvinylpyrrolidone, polyethylene glycol, polyethylene oxide, polyvinyl alcohol, silicon dioxide, surfactant, mixed surfactant/wetting agent, emulsifier, and mixtures thereof.

4. The solid oral dosage form of claim 3, wherein the gelling agent is selected from the group consisting of sodium carboxymethylcellulose, methylcellulose, ethylcellulose, hydroxyethylcellulose, hydroxypropylcellulose, hydroxypropylmethylcellulose, alginate, carrageenan, gum tragacanth, gum acacia, guar gum, xanthan gum, pectin, polyethylene oxide, polyvinyl alcohol, and mixtures thereof.

5. The solid oral dosage form of claim 4, wherein the gelling agent comprises alginate.

6. The solid oral dosage form of claim 5, wherein the gelling agent further comprises xanthan gum.

7. The solid oral dosage form of claim 6, wherein the gelling agent further comprises hydroxypropylmethylcellulose.

8. The solid oral dosage form of claim 1, wherein the opioid analgesic is morphine sulfate.

9. The solid oral dosage form of claim 1, wherein the opioid analgesic is oxycodone hydrochloride.

10. The solid oral dosage form of claim 9, wherein the controlled release material comprises an acrylic polymer.

11. A solid oral dosage form comprising:
(a) an inert tamper resistant core comprising an inner component and an outer component coated on the inner component, wherein the inert tamper resistant core comprises a gelling agent comprising xanthan gum; and
(b) a coating surrounding the inert tamper resistant core, the coating comprising an opioid analgesic dispersed in a controlled release material,
wherein the opioid analgesic is selected from the group consisting of morphine, codeine, oxycodone, hydrocodone, hydromorphone, oxymorphone, and pharmaceutically acceptable salts thereof,
wherein the coating provides a controlled release of the opioid analgesic for a time of at least 12 hours,
wherein the inert tamper resistant core does not include the opioid analgesic, and
wherein the solid oral dosage form is a tablet comprising a single coated core that comprises a therapeutically effective amount of the opioid analgesic.

12. The solid oral dosage form of claim 11, wherein the inert tamper resistant core comprises an additional gelling agent.

13. The solid oral dosage form of claim 12, wherein the additional gelling agent is selected from the group consisting of sugar, sugar derived alcohols, mannitol, sorbitol, starch, microcrystalline cellulose, sodium carboxymethylcellulose, methylcellulose, ethylcellulose, hydroxyethylcellulose, hydroxypropylcellulose, hydroxypropyl methylcellulose, attapulgite, bentonite, dextrin, alginate, carrageenan, gum tragacanth, gum acacia, guar gum, pectin, gelatin, kaolin, lecithin, magnesium aluminum silicate, carbomer, carbopol, polyvinylpyrrolidone, polyethylene glycol, polyethylene oxide, polyvinyl alcohol, silicon dioxide, surfactant, mixed surfactant/wetting agent, emulsifier, and mixtures thereof.

14. The solid oral dosage form of claim 13, wherein the additional gelling agent is selected from the group consisting of sodium carboxymethylcellulose, methylcellulose, ethylcellulose, hydroxyethylcellulose, hydroxypropylcellulose, hydroxypropylmethylcellulose, alginate, carrageenan, gum tragacanth, gum acacia, guar gum, pectin, polyethylene oxide, polyvinyl alcohol, and mixtures thereof.

15. The solid oral dosage form of claim 14, wherein the additional gelling agent comprises alginate.

16. The solid oral dosage form of claim 15, wherein the additional gelling agent further comprises hydroxypropylmethylcellulose.

17. The solid oral dosage form of claim 16, wherein the controlled release material comprises an acrylic polymer.

18. The solid oral dosage form of claim 11, wherein the opioid analgesic is morphine sulfate.

19. The solid oral dosage form of claim 11, wherein the opioid analgesic is oxycodone hydrochloride.

20. The solid oral dosage form of claim 11, wherein the inert tamper resistant core has a breaking strength of at least 400 Newtons.

21. A solid oral dosage form comprising:
(a) an inert tamper resistant core comprising an inner component and an outer component coated on the inner component, wherein the inert tamper resistant core comprises a gelling agent comprising a mixture comprising xanthan gum, hydroxypropylmethylcellulose, and alginate; and
(b) a coating surrounding the inert tamper resistant core, the coating comprising an acrylic polymer and an opioid analgesic selected from the group consisting of morphine, codeine, oxycodone, hydrocodone, hydromorphone, oxymorphone, and pharmaceutically acceptable salts thereof, wherein the opioid analgesic is dispersed in the acrylic polymer, wherein the coating provides a controlled release of the opioid analgesic for a time of at least 12 hours,
wherein the inert tamper resistant core does not include the opioid analgesic,
wherein the solid oral dosage form is a tablet comprising a single coated core that comprises a therapeutically effective amount of the opioid analgesic.

22. The solid oral dosage form of claim 21, wherein the inert tamper resistant core has a breaking strength of at least 400 Newtons.

23. The solid oral dosage form of claim 22, wherein the opioid analgesic is morphine sulfate or oxycodone hydrochloride.

24. A solid oral dosage form consisting of:
(a) an inert tamper resistant core having a breaking strength of at least 400 Newtons, wherein the inert tamper resistant core comprises an inner component and an outer component coated on the inner component; and
(b) a coating surrounding the inert tamper resistant core, wherein the coating comprises an opioid analgesic dispersed in
a controlled release coating,
wherein the controlled release coating provides a controlled release of the opioid analgesic for a time of at least 12 hours,
wherein the inert tamper resistant core does not include the opioid analgesic, and
wherein the solid oral dosage form is a tablet comprising a single coated core that comprises a therapeutically effective amount of the opioid analgesic.

* * * * *